United States Patent [19]

Inoue et al.

[11] Patent Number: 5,674,498
[45] Date of Patent: Oct. 7, 1997

[54] BLOOD-LIPID DEPRESSANT AND VICTUALS CONTAINING THE SAME

[75] Inventors: Shuji Inoue; Masato Egawa, both of Kanagawa; Susumu Shimura, Saitama; Yoshio Itoh, Tokyo, all of Japan

[73] Assignee: Lotte Co., Ltd., Tokyo, Japan

[21] Appl. No.: 494,316

[22] Filed: Jun. 23, 1995

[30] Foreign Application Priority Data

Jun. 23, 1994 [JP] Japan .................................. 6-141874

[51] Int. Cl.$^6$ .................................................. A61K 35/78
[52] U.S. Cl. .......................................... 424/195.1; 514/824
[58] Field of Search .......................... 424/195.1; 514/824

[56] References Cited

PUBLICATIONS

Chem. Abstrs. 72:51792d, "Chemical Examination of the Leaves of Cassia mimosoides", S. Sankara, et al. 1970.
Chem. Abstrs. 107:200371m, "A New Anthraquinone Pigment From Cassia minomosoides Linn", K. Mukherjee, et al. 1987.
Chem. Abstrs. 106:172977x, "Phytochemical Investigation of Cassia mimosoides Linn", P. Bhattacharya, et al. 1987.

Chem. Abstrs. 120:50142q, "Lipase Inhibitors in Cassia mimosoides L. var. nomame Makino", S. Shimura, et al. Jan. 3, 1994.

*Primary Examiner*—John W. Rollins
*Attorney, Agent, or Firm*—Young & Thompson

[57] ABSTRACT

In a blood-lipid depressant for depressing a blood-lipid level, an effective component of the depressant is an extract extracted with an extracting solvent from a senna species (*Cassia mimosoides* L. var. *nomame* Makino). An effective component of the depressant is an extract obtained by fractionating via chromatographic methods an extract extracted with an extracting solvent from a senna species (*Cassia mimosoides* L. var. *nomame* Makino).

4 Claims, No Drawings

BLOOD-LIPID DEPRESSANT AND VICTUALS CONTAINING THE SAME

BACKGROUND OF THE INVENTION

1. Field of the Invention

The present invention relates to a blood-lipid depressant for prevention and treatment of hyperlipidemia and processed foods containing the same.

2. Description of the Related Art

Recently, peoples have been taking foods with high contents of lipids due to luxuriation of diet and westernization of eating habit, in consequence of which the number of patients suffering from hyperlipidemia has been on the increase.

Hyperlipidemia is a disease accompanying several disorders, wherein one or more components of intraserous lipids, for example, cholesterol, triglyceride, phospholipids and free fatty acids are increased. Hyperlipidemia may be classified into two large groups of hypercholesterolemia and hypertriglyceridemia.

Many medicines besides pravastatin have been developed and used as a remedy for depressing serum cholesterol. For hypertriglyceridemia, bezafibrate, pantethine, dextran sodium sulfate and others have been used in therapy. In the Japanese Laid-open Patent Application No. 55-98114, the use of lasalocids as a remedy is disclosed.

In fact, those remedies have anti-hyperlipidemia effects, but not preferable to be used easily and daily by persons in health because of often appearance of several side effects.

In relation to extracts from natural substances which may be free from any side effect, the Japanese Laid-open Patent Application No. 2-88525 discloses that a water-soluble extract of an oak species (*Quercus salicina*) depresses cholesterol and triglyceride levels in serum. Further, the Japanese Patent Publication No. 1-144957 discloses that the use of a gardenia extract together with soybean saponin also depresses the cholesterol and triglyceride levels. Moreover, the Japanese Laid-open Patent Application No. 64-22820 discloses genipin which is a component from a gardenia may also depress total cholesterol and triglyceride levels. Furthermore, the Japanese Laid-open Patent Application No. 5-255100 discloses improvement in hyperlipidemia by a kind of phytic acids contained in rice bran etc. The effects provided by those extracts are, however, insufficient.

SUMMARY OF THE INVENTION

Accordingly, an object of the present invention is to provide drugs and processed foods which can act steadily to depress the level of blood-borne lipids (hereinafter "a blood-lipid level").

A further object of the present invention is to provide drugs and processed foods which can be useful in a daily life.

A furthermore object of the present invention is to provide drugs and processed foods which can be safely taken over a long term.

The above and other objects, features and advantages of the present invention will be apparent from the following descriptions.

The present invention provides a blood-lipid depressant for depressing a blood-lipid level wherein an effective component of the depressant is an extract extracted with an extracting solvent from a senna species (*Cassia mimosoides* L. var. *nomae* Makino).

The present invention also provides a blood-lipid depressant for depressing a blood-lipid level wherein an effective component of the depressant is an extract obtained by fractionating via chromatographic methods an extract extracted with an extracting solvent from a senna species (*Cassia mimosoides* L. var. *nomae* Makino).

The present invention also provides a processed victual for depressing a blood-lipid level wherein the victual contains an extract extracted with an extracting solvent from a senna species (*Cassia mimosoides* L. var. *nomae* Makino).

The present invention also provides a processed victual for depressing a blood-lipid level wherein the victual contains a fractionated extract obtained by fractionating via chromatographic methods an extract extracted with an extracting solvent from a senna species (*Cassia mimosoides* L. var. *nomae* Makino), hereinafter "*Cassia nomame*".

DISCLOSURE OF THE INVENTION

As a result of earnest studies on the natural plants with excellent safety, the inventors have confirmed that a water or organic solvent extract from a senna species (*Cassia nomame*) and a chromatographic fraction of the extract function to depress cholesterol and triglyceride levels in blood.

Namely, the present invention provides a blood-lipid depressant and processed foods and drinks containing the depressant, wherein an effective component of said depressant is an extract obtained from a senna species (*Cassia nomae*) by extracting with water and/or organic solvents, and/or is a fractionated product obtained from said extract by chromatographic fractionation.

A senna species (*Cassia nomae*) has been used for gastrointestinal health as a crude drug, "Sanpenzu", and provided with excellent safety for beverage as a substitution of such teas named "Mame-cha", "Kōbō-cha" and etc. from a long time ago.

A whole grass (land-surface portion dried) of the senna species (*Cassia nomame*) is cut into fragments or crushed with a proper crusher like a mill. The resultant fragments or pieces are subjected to extraction with water, organic solvents or mixture thereof to obtain an extract.

Methanol, ethanol, propanol, butanol, ether, acetone, hexane, chloroform, toluene, ethyl acetate, and tetrahydrofuran are available as the organic solvent whereas one or more solvents may be selected from those to be used, ethanol, acetone and ethyl acetate are preferable in the view point safety. Especially, the use of ethanol is more preferable as generally provided for beverage. It is furthermore preferable to use ethanol as a mixture with water at a proper proportion.

The extraction may be carried out by the following method. *Cassia nomae* and 1–50 liter, preferably 10 liter of the extractive solvent to 1 Kg of the fragment of the senna species are mixed in a vessel having a stirrer, stood for a predetermined term, e.g. over night with a moderate stirring and a filtrate collected from the resultant mixture is dried under reduced pressure. In the extraction, a heated solvent may be used.

The resultant extract is a paste or a powder with color of light brown or brown and could be used as a blood-lipid depressant directly or after purified. Namely, the extract may be subjected to chromatography to obtain a purified fraction thereof.

Applicable chromatographies are a liquid chromatography, an adsorption chromatography, an ion exchange chromatography and a partition chromatography. The fractionated extract is obtained by means of those chromatographies using the extractive solvent.

The yield of the fractionated extract is about 20–40 g by dry weight per 1 Kg of the fragments of the senna species (*Cassia nomame*).

The resultant extract and fractionated extract are diluted with a proper solvent or concentrated for those use. Further, the extracts are pasted or powdered through an operation of suction or lyophilization for those use. Moreover, the extract and fractionated extract may be filled in capsules or may be formed for easy administration in soft capsules or tablets, granule and etc. Alternatively, the extract and fractionated extract may also be provided as processed foods and drinks by mixing with materials for victuals. When mixed with the materials for victuals, it is preferable to carry out the mixture at a proportion of 0.5–2.5% to the materials.

Further, those extract and fractionated extract may be occasionally used as the mixture thereof though usually used individually.

The present invention provides the following advantages.

A blood-lipid depressant according to the present invention shows a remarkable depressive function to the blood-lipid levels particularly in triglyceride and cholesterol.

The material for the blood-lipid depressant according to the present invention may be a plant used for beverage. The depressant, therefore, has excellent safety.

The blood-lipid depressant according to the present invention has no strong bitter nor bad taste as well as no destructive effect on the original taste of foods, confectionery and drinks.

Whereas modifications of the present invention will be apparent to a person having ordinary skill in the art, to which the invention pertains, it is to be understood that embodiments show and described below are by no means intended to be a limiting sense. Accordingly, it is to be intended to cover by claims any modifications which fall within the spirit and scope of the present invention.

EXAMPLES

Example 1

The whole grass (land-surface portion dried) of a senna species (*Cassia nomame*) was crushed and per 0.8 Kg of which, 8 liters of 40% ethanol solution were added followed by standing over night with an occasional stirring. The resultant mixture was filtered. The filtrate was dried under a reduced pressure and then dissolved in 30% ethanol solution to be fed on a Diaion HP20 column (10 cm internal diameter and 38 cm length, commercially available from Mitsubishi Kasei Co. Ltd.). After washed with 15 liters of 30% ethanol solution, an elution was carried out with 10 liters of 80% ethanol solution. Such fractions as eluted by the ethanol solution with the concentration of 30–80% were collected. The yield of this fractions was about 28 g by dry weight. The product had 57% of phenol content on Folin-ciocalteu reagent with the standard of (−)-epicatechin, from which it was confirmed that phenolic substances were predominant in the product.

Examination 1

Female Sprague-Dawley rat with 265–298 g of initial body weight were used as samples. The rat were individually bred in stainless cages under the conditions of 24°±2° C. and 12 hours day-night cycle (8:00–20:00; daytime). The rat were grouped into a control group and a medicated group. The control group was fed with a high-fat diet shown on the table 1 while the medicated group was further grouped into 4 subgroups, each of which was fed with high-fat diets added with 0.5–2.5% of the senna species fraction prepared in the example 1.

TABLE 1

| Composition of the High-Fat Diet | |
| --- | --- |
| Lard | 58 (%) |
| Fish Powder | 30 |
| Delipidated Soybean Powder | 10 |
| Vitamin/Mineral Mixture | 2 |

After a week from the beginning of feeding, bloods were drawn from cervical veins under etherization so that serum compositions at ad lib feeding were measured. After two weeks from the beginning of feeding, the blood collection and the measurement were carried out similarly to the above following to 12 hours of fasting. In the measurement of the serum compositions, the glucose oxidase method was used for glucose, a dry chemical analyzer was used to measure the total cholesterol, triglyceride, GOT and GPT.

The table 2 shows the serum compositions at ad lib feeding after a week from the beginning of the feeding.

TABLE 2

Effects of Fractionated extracts from the Senna species (*Cassia nomae*) on Serum Compositions
(One week feeding, ad lib feeding)

| Fractionated extracts from the Senna species (%/diet) | Total Cholesterol (mg/dl) | Triglyceride (mg/dl) | Glucose (mg/dl) | GOT (IU/dl) | GPT (IU/dl) |
| --- | --- | --- | --- | --- | --- |
| 0 (Control) | 68.8 ± 10.7* | 344 ± 68 | 179 ± 11 | 90.8 ± 8.6 | 47.0 ± 3.0 |
| 0.5 | 48.4 ± 4.8 | 212 ± 43 | 200 ± 6 | 74.2 ± 3.4 | 19.4 ± 1.2 |
| 1.0 | 58.6 ± 9.9 | 205 ± 49 | 148 ± 8 | 57.4 ± 1.0 | 24.6 ± 1.8 |
| 1.5 | 33.6 ± 8.2 | 106 ± 31 | 144 ± 11 | 59.2 ± 4.9 | 19.4 ± 1.5 |
| 2.5 | 48.2 ± 4.1 | 98 ± 24 | 165 ± 2 | 62.4 ± 3.6 | 21.0 ± 2.4 |

*Mean ± S.E. (n = 5)

Among serous lipids, triglyceride level in the group with the dosage of 0.5% was lower than that in the control group. Especially, in the groups with the dosages of 1.5 and 2.5%, a remarkable depression of the triglyceride level was observed. Further, total cholesterol level in each medicated group was low, especially in the group with the dosages of 1.5, a remarkable depression thereof was observed. Moreover, blood glucose levels (Glucose) in the groups with the dosages of 1.0% or more were also lower than that of the control group. Furthermore, GOT and GPT, which are the parameters of hepatopathy, were lower in any medicated groups than that in the control group.

The table 3 shows the serum compositions under 12 hours fasting after two weeks feeding.

TABLE 3

Effects of Fractionated extracts from the Senna species (*Cassia nomae*) on Serum Compositions
(two weeks feeding, under 12 hours fasting)

| Fractionated extracts from the Senna species (%/diet) | Total Cholesterol (mg/dl) | Triglyceride (mg/dl) | Glucose (mg/dl) | GOT (IU/dl) | GPT (IU/dl) |
| --- | --- | --- | --- | --- | --- |
| 0 (Control) | 50.6 ± 5.6* | 89.2 ± 18.2 | 139 ± 14 | 79.8 ± 4.3 | 21.0 ± 2.0 |
| 0.5 | 48.4 ± 4.3 | 58.6 ± 6.7 | 136 ± 6 | 78.2 ± 7.6 | 17.6 ± 4.7 |
| 1.5 | 33.6 ± 5.1 | 30.8 ± 2.4 | 128 ± 6 | 63.6 ± 6.2 | 15.0 ± 2.2 |

*Mean ± S.E. (n = 5)

Triglyceride levels in the groups medicated with the dosages of 0.5 or 1.5% were lower than in the control group, and the cholesterol level in the group medicated with the dosage of 1.5 was low.

From the above results, it was confirmed that the extracted and fractionated product from the senna species (*Cassia nomame*) shows a function of a remarkable depression of the blood triglyceride level and blood total cholesterol level, namely, effective depression of lipids in blood.

Example 2

The whole grass (land-surface portion dried) of a senna species (*Cassia nomame*) was crushed and per 1.0 Kg of which, 50 liters of water were then added followed by standing over night with an occasional stirring. The resultant mixture was filtered. The filtrate was dried under a reduced pressure and then dissolved in 20% acetone solution to be fed on a Diaion HP 20 column (10 cm internal diameter and 38 cm length, commercially available from Mitsubishi Kasei Co. Ltd.). After washed with 30 liters of 20% acetone solution, an elution was carried out with 20 liters of 70% acetone solution. Such fractions as eluted by the acetone solution at a concentration of 20–70% were collected. The yield of this fractions was about 30 g by dry weight. The product had 52% of phenol content on Folin-ciocalteu reagent with the standard of (−)-epicatechin, from which, it was confirmed that phenolic substances were predominant in the product.

Example 3

The whole grass (land-surface portion dried) of a senna species (*Cassia nomame*) was crushed and per 1.0 Kg of which, 5 liters of acetone were then added followed by standing over night with occasional stirring in an airtight condition. The resultant mixture was filtered. The filtrate was dried under a reduced pressure thereby about 41 g of the extract powder was obtained.

Example 4

Approximately 12 g of the extract powder was obtained by the same manner as the example 3 except using 10 liters of hexane.

Example 5

Approximately 53 g of the extract powder was obtained by the same manner as the example 3 except using 10 liters of ethyl acetate.

Example 6

Approximately 53 g of the extract powder was obtained by the same manner as the example 3 except using 10 liters of tetrahydrofuran.

Example 7

Approximately 106 g of the extract powder was obtained by the same manner as the example 3 except using 10 liters of chloroform-methanol (2:1) mix solvent.

The following examples are directed to applications of the above depressant to foods and drinks.

Example 8

There were mixed 40 g of lactose, 19 g of corn starch, 40 g of the fractionated extract from the senna species (*Cassia nomame*) prepared in the example 1 and 1 g of sugar ester. The mixture was then granulated using an extruding granulater for subsequent compression and molding thereof by a conventional method using a tablet machine to thereby produce 100 tablets of the blood-lipid depressant as non-coated tablets.

These tablets contain 400 mg/tablet of the fractionated extract from the senna species (*Cassia nomame*).

Example 9

There were fed into a mixer 3.5 Kg of cacao mass, 1.5 Kg of cacao butter, 0.45 Kg of whole milk powder, 4.5 Kg of sugar and 50 g of the fractionated extract from the senna species (*Cassia nomame*) obtained by the method of the example 1 and 1 g of sugar ester. After mixed for 30 min. at 38°–43° C., the mixture was transferred to a refiner to be uniformly refined into microparticles with a size of below 40 μm. The particles were then transferred into a canting machine to be stirred and mixed with heating up to about 60° C. for 40 hours. Just before the discontinuation of the canting, 50 g of lecithin as an emulsifier and a little amount of a flavor were added followed by a homogenization thereof and subsequent tempering at 27°–32° C. Further, this mixture was then transferred into a mold to be cooled and caked to thereby be made into a chocolate. The chocolate was fine in taste and shows a function to depress the blood-lipid.

Example 10

There were kneaded 500 g of gum base, 1.2 Kg of sugar, 200 g of starch syrup, 20 g of softener/colorant, 20 g of acidulant, 20 g of flavor and 20 g of the fractionated extract from the senna species (*Cassia nomame*) obtained by the method of the example 1 so as to be made into a chewing gum via the a conventional process. The chewing gum obtained was fine both in texture and taste and depressive to the blood-lipid.

Example 11

There were used, to prepare a dough, 1 Kg of wheat flour, 100 g of corn starch, 250 g of sugar, 125 g of margarine, 5 g of sodium chloride, 25 g of sodium carbonate, 8.8 g of ammonium carbonate, 6.3 g of soybean lecithin, 75 g of a whole egg, 6.3 g of vanilla oil, 41 g of the fractionated extract from the senna species (*Cassia nomame*) and 250 g of water. Following to spreading, the dough was molded and roasted to be made into a biscuits being depressive to the blood-lipid with good hardness and taste.

Example 12

There were mixed and boiled down to 120° C, 150 g of sugar, 150 g of starch syrup, 60 g of condensed milk, 18.8 g of wheat flour and 2 g of the fractionated extract from the senna species (*Cassia nomame*). The mixture was then added with 2.2 g of butter, 1.6 g of cacao butter, 2.2 g of coconut oil and 1 g of flavor for stirring thereof and subsequent cooling and molding to thereby be made into caramels. The caramels had a good melting property in mouth and a depressing effect on the blood-lipid level.

Example 13

There was added to 1 liter of green tee 0.5 g of the fractionated extract from the senna species (*Cassia nomame*) to thereby be made into a green-tee beverage with an enhanced function of depressing the blood-lipid level.

What we claim are:

1. A foodstuff comprising 0.5–2.5% by weight of dried extract of *Cassia nomame*, in intimate admixture with an edible foodstuff.

2. A foodstuff according to claim 1, wherein said extract is the dried chromatographic fraction having an eluant alcohol concentration ranging from about 30–80%, following alcohol extraction of *Cassia nomame*.

3. A foodstuff according to claim 1, wherein said extract is the dried chromatographic fraction having an eluant acetone concentration ranging from about 20–70%, following alcohol extraction of *Cassia nomame*.

4. A foodstuff containing 0.5–2.5% by weight of a dried extract of *Cassia nomame*, in intimate admixture with an edible foodstuff material, said dried extract having been partially purified by a chromatographic method wherein an eluant by an alcohol solution is collected on condition that the alcohol concentration of the eluant ranges within about 30–80%, or wherein an eluant by an acetone solution is collected on condition that the acetone concentration of the eluant ranges within about 20–70%.

* * * * *